United States Patent [19]

Ginsburg et al.

[11] Patent Number: 5,775,900
[45] Date of Patent: Jul. 7, 1998

[54] METHOD OF PRODUCING A CLEAR STENT FOR THE EDENTULOUS IMPLANT PATIENT AND APPARATUS THEREFOR

[76] Inventors: Stephen J. Ginsburg, 9 Everett St., Wellesley, Mass. 02181; Neil N. Cavalier, 28 Lockeland Rd., Winchester, Mass. 01890

[21] Appl. No.: 685,831

[22] Filed: Jul. 25, 1996

[51] Int. Cl.$^6$ ................................................. A61C 3/00
[52] U.S. Cl. .................. 433/75; 433/171; 433/173; 433/213
[58] Field of Search ................... 433/213, 171, 433/173, 75

[56] References Cited

U.S. PATENT DOCUMENTS

| | | | |
|---|---|---|---|
| 4,227,877 | 10/1980 | Tureaud et al. | 433/37 |
| 4,361,528 | 11/1982 | Ginsburg et al. | 264/28 |
| 4,413,979 | 11/1983 | Ginsburg et al. | 433/41 |
| 5,304,063 | 4/1994 | Ginsburg | 433/199.1 |
| 5,403,186 | 4/1995 | Ginsburg | 433/199.1 |

OTHER PUBLICATIONS

Turbyfill, W.F.; The Successful Mandibular Implant Denture—Part One Dental Economics, Dec. 1995, pp. 70–71.
Hobo, Sumiyama, et al., Osseointegration and Occlusal Rehabilitation, 1991 Quintessence Publishing Co., pp. 65–73.

*Primary Examiner*—John J. Wilson
*Attorney, Agent, or Firm*—Sherman and Shalloway

[57] ABSTRACT

A clear thermally deformable surgical or diagnostic stent which can be fitted to a fully or partially edentulous ridge and the surrounding tissue surfaces and a method of producing and fitting stents using their thermally deformable characteristics. A kit comprising a matched pair of a clear thermally deformable surgical or diagnostic stent and an identical thermally deformable interim or temporary denture and a method of producing and fitting the stent and denture using their thermally deformable characteristics. The stent and denture are formed from a doughy mixture of a plasticized liquid monomer and a methyl methacrylate polymer in a ratio of 1:3–3.5 parts by weight. When heated to a temperature above 120° F. (49° C.) the stent and denture are malleable and may be molded in the mouth or on a model of the patient to attain an approximation of the tissue surfaces.

33 Claims, 6 Drawing Sheets

METHOD OF PRODUCING A CLEAR STENT FOR THE EDENTULOUS IMPLANT PATIENT AND APPARATUS THEREFOR

FIELD OF THE INVENTION

This invention relates generally to the field of implant prosthodontics whereby the edentulous patient's dentition is restored by means of an implant retained or implant supported prosthesis—either fixed or removable. More precisely, it involves a method of producing and utilizing a thermoplastic clear acrylic resin prefabricated surgical and/or radiographic stent (also termed a surgical and/or radiographic template) which retains its molded form to a high degree of accuracy in an efficient and economical manner. Furthermore, this invention presents a kit whereby the dental practitioner is provided with the necessary elements to produce a surgical and/or radiographic stent, a fully aligned and functioning interim or temporary denture and to take appropriate dentulous and edentulous impressions for use in preparing a permanent prosthesis.

BACKGROUND OF THE INVENTION

Molding and flasking methods and techniques for producing conventional stents and dentures are well known in the prior art. However, the preparation of these conventional elements is an expensive, time consuming process, usually requiring a pre-existing or newly fabricated prosthesis and requiring multiple visits to an experienced dentist and extensive preparation in a dental laboratory. Often, this essential step in the diagnostic process of implant prosthodontics is foregone for financial and/or time related reasons.

However, in order to fabricate implant retained and/or supported prostheses for the totally or partially edentulous patient, the dentist must incorporate a stent in the diagnostic and implant placement phase of treatment. This is important to, firstly, locate the ideal final tooth position suitable to meet the patient's esthetic and functional needs which directly leads to, secondarily, the anatomically correct positioning of the implant fixtures by the surgeon. Typically, this procedure involves a number of clinical and laboratory appointments involving impression making (preliminary and final), fabrication of final impression trays, making of master casts on which the removable prosthesis or stents are fabricated, making of record bases with wax occlusion rims used to relate these master casts on an articulator utilizing appropriate maxillo-mandibular relation records, arranging artificial teeth, the verification of the esthetic and mechanical placement of said teeth, and finally the fabrication of a surgical and/or radiographic stent used for locating the ideal position for implant placement.

Accordingly, there is a need in the art for an economical stent that is constructed of a material that has properties which enable it to serve dual purposes as both a radiographic measuring device and a surgical guide template. Radiographic stents are acrylic resin forms used to make presurgical, diagnostic radiographs so that accurate bone measurements can be made. These radiographic stents are clear acrylic resin forms, adapted to the maxilla and/or mandible, in which steel ball bearings (or other suitable radio-opaque markers) with a precise known dimension are imbedded. This is done in the anticipated locations for implant placement. With such a device radiographs are made which allows one to determine the true available bone height and, as a result, the correct implant length to be used. This radiographic stent may serve the dual purpose of a surgical guide stent. A surgical guide stent is obligatory for determining both the location and direction for implant fixture insertion and is once again used during the second surgical procedure of uncovering the implant fixtures. This stent is essential for proper implant fixture placement. It aids and guides the surgeon in positioning implant fixtures as ideally as possible.

Concurrently with the preparation of a surgical and/or radiographic stent, it is preferable to provide the patient with a temporary denture which fits in proper intraoral relationship in the patient's mouth. This is important to locate the ideal final tooth positions suitable to meet the patient's esthetic and functional needs and leads directly to the anatomically correct positioning of the implant fixtures. Typically, denture fabrication, whether temporary or permanent, involves a number of clinical and laboratory appointments for preliminary impressions, construction of custom impression trays, final impression making, fabrication of record bases with wax occlusion rims on master casts, arranging of artificial teeth, verification of tooth arrangement, processing of the denture into acrylic resin and, finally, duplication to act as the surgical or radiographic stent. Throughout the time all of these steps are occurring, the patient is often without a properly fitting denture and suffers both esthetically and functionally as a result.

Accordingly, there is a need in the art for a system or kit which provides the dental practitioner with the means to prepare a surgical and/or radiographic stent to be used to locate dental prosthetic implants and to concurrently prepare and provide the patient with an interim denture for use until the final permanent prosthesis is in place. There is also a need to be able to prepare the stent and the interim denture early on in the process and, preferably, during a single preliminary visit.

The inclusion in a single kit of a moldable temporary denture and an identical moldable stent, both of which can be adjusted and fitted to the patient during the same visit to the dentist and without the need for repeated impressions, castings and fittings, further reduces the number of intermediary clinical and laboratory steps and the costs associated therewith.

The purpose of this invention is to eliminate various intermediate clinical and laboratory steps in the procedure list of implant radiographic and/or surgical stent and temporary denture fabrication. This is accomplished by fabricating diverse stents (essentially small, medium and large base sizes with various tooth arrangements on each base size) in clear thermoplastic acrylic resin. The resin prosthetic stent may be placed in water of 120°–160° F. (49°–71° C.) for approximately two minutes allowing it to become moldable. The appropriate prosthetic stent may then be formed in the patient's correct anatomical configuration either on a model or intraorally. Once formed and subsequently chilled, the base becomes stable. Tooth position and esthetics may be verified and corrected if need be since the thermoplastic stent may be re-heated, remolded and adjusted any number of times. Once satisfied with the esthetic and mechanical parameters, the clear preformed prosthetic stent is able to act as a surgical and/or radiographic stent.

In addition, diverse temporary or interim dentures identical, to the stents, are fabricated using the same molds and materials such that at least the denture base is a moldable thermoplastic acrylic resin colored to resemble the gum tissues. Like the stent, the resin of the denture may be placed in water of 120°–160° F. (49°–71° C.) for approximately two minutes allowing it to become moldable. The denture may then be formed to the patient's correct anatomical configuration and subsequently cooled to become stable. The teeth of the denture are preferably made of a harder acrylic and are mounted in the denture base in a manner which permits them to be individually adjustable while the base is at its moldable temperature. In this manner, the denture teeth may be properly positioned for optimum interdigitation with opposing existing teeth or dentures.

The advantage of the method of implant stent and interim denture fabrication and the provision of kits comprising identical paired stents and dentures is a reduced number of intermediary steps, both clinical and laboratory, cost as well as ease of technique.

SUMMARY OF THE INVENTION

Disclosed and claimed herein is a thermally deformable clear acrylic resin removable prosthetic stent which is configured to form a full or partial removable prosthesis. The stent is clear in order to facilitate visualization of the underlying supporting tissues. It is fabricated from a radiolucent material in order to visualize radio-opaque structures of interest such as the markers located within the stent as well as the important bony anatomy of the patient's oral cavity. The inner surface of the clear stent can be adapted and coated with a polymerizable liner to intimately conform to the details of the edentulous ridge and the surrounding tissues of the patient's mouth if the operator so wishes. The outer surface is in the form of teeth and can be adapted to support tooth arrangements. The prosthetic stent is formed by a dental molding process from a doughy mixture comprising 1 part by weight of a plasticized liquid monomer and 3–3.5 parts by weight of a methyl methacrylate polymer powder. The stent material is thermally deformable at a temperature above 120° F. (49° C.) and enables the prosthetic stent to cure in the patient's mouth in an impression-taking position without distorting the impression recess upon removal from the mouth. Likewise, the operator may configure and mold the stent material on an available model of the patient. The stent is made available in various sizes, shapes and tooth arrangements allowing it to be fit to a wide range of maxillary and mandibular configurations.

Also disclosed and claimed herein is a kit comprising a thermally deformable clear acrylic resin removable prosthetic stent and a duplicate partially preformed interim denture. The stent and denture utilize identical bases and molds of artificial teeth and are prefabricated in a range of base sizes, i.e., small, medium and large, with various tooth arrangements. Each kit contains a stent and denture which are identical in size and tooth arrangement so that the practitioner has the availability of the stent and a matching interim denture right from the initial diagnostic appointment. The kit may include a selection of moldable custom fit dental impression trays for use in taking impressions of the patient's dentulous or edentulous ridge concurrently with the molding of the stent and temporary denture. In addition, the kit may include unpolymerized resin liners pre-sized to line the inner surfaces of the stent and denture to maximize the fitting process.

The stent and denture are also provided in the form of a tooth arch from which partial segments may be cut by the dentist. In this embodiment, the stent and denture are formed with only enough base structure to provide support for the teeth. The same molding methods and materials are employed to fabricate this embodiment.

The prosthetic stent and at least the base of the matching denture are formed by a dental molding process from a doughy mixture comprising 1 part by weight of a plasticized liquid monomer and 3–3.5 parts by weight of a methyl methacrylate polymer powder. This material is thermally deformable at a temperature above about 120° F. (49° C.) and enables the stent and denture to cure in the patient's mouth in an impression taking position. In addition, the inner surfaces of the stent and denture can be adapted and coated with the polymerizable liner to intimately conform to the patient's edentulous ridge and mouth tissues.

DETAILED DESCRIPTION OF THE INVENTION

Figure 1:
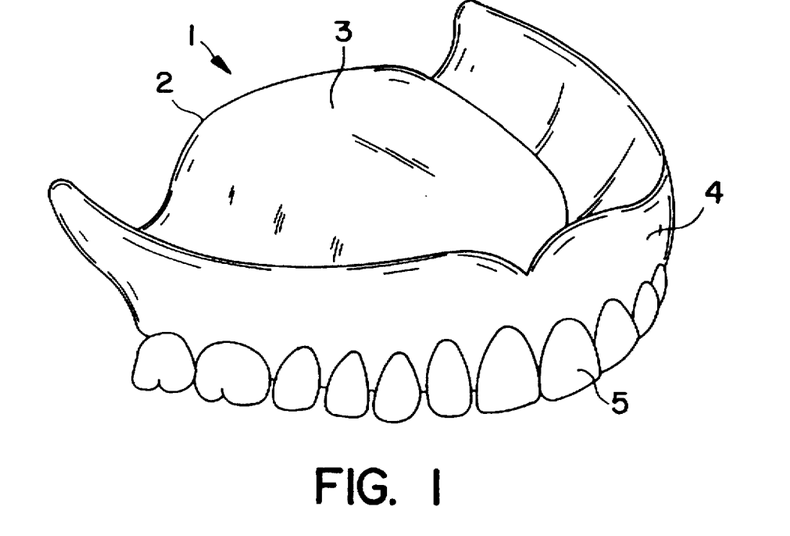
FIG. 1 is an oblique view of the clear maxillary radiographic/surgical stent showing the inner surface.

Referring now to the drawings and, in particular to FIG. 1, there is shown a clear maxillary radiographic/surgical stent 1 of the present invention comprising a base 2 having an inner surface 3 and an outer surface 4. The inner surface 3 of stent 1 is configured to approximate the edentulous ridge and the surrounding interior contours of the intraoral tissues of the patient's mouth. The outer surface 4 resembles the gum surface and includes one or more teeth 5. The base 2 is made of a clear material in order to visualize the underlying structures of the patient's mouth. The teeth 5 may be separate elements embedded in the material of the base 2, but are preferably formed as an integral part of the base 2 and from the same clear material.

Figure 5:
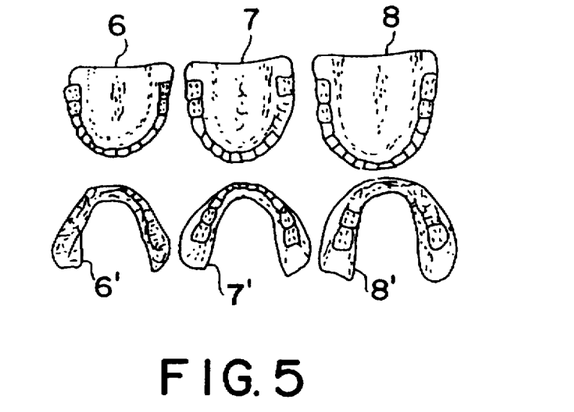
FIG. 5 shows a selection of three sets of stents and/or dentures providing maxillary and mandibular units in approximate small, medium and large sizes.
Figure 6:
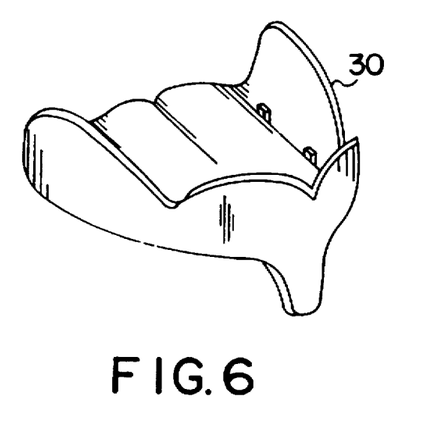
FIG. 6 shows a moldable maxillary impression tray includable as part of the kit.

The properties of the stent 1 of the present invention are such that it is rendered malleable at approximately 120° F. (49° C.) thereby allowing the stent 1 to be molded in the mouth of a patient or, if desired, on a model to attain an approximation of the tissue surfaces therein. Although the stent shown in FIG. 1 is for a maxillary edentulous ridge, it is understood that the present invention is equally applicable for the mandibular edentulous, maxillary partially edentulous, and mandibular partially edentulous ridge. Maxillary and mandibular forms are shown in FIG. 5. The moldable properties of the stent 1 also allow the outer surface 4 of the stent 1 to be molded concurrently with the attainment of an approximation of the ridge surfaces. This permits the relative arrangement of the teeth 5 to be altered to accommodate a patient's specific intraoral structure. Such adjustment is extremely important in accurately locating the positions for implantable prosthetic supports. This is particularly the case in partially edentulous patients where the stent 1 is used to locate the position of an implant relative to both adjacent teeth along the same maxillary or mandibular ridge and opposing teeth for accurate interdigitation.

Figure 2:
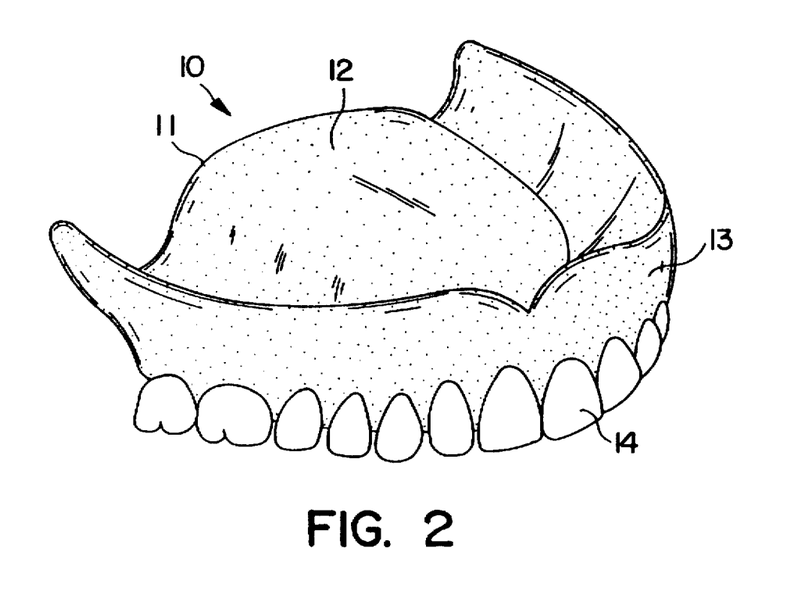
FIG. 2 is an oblique view of a matching maxillary temporary denture showing the inner surface.

Referring now to FIG. 2, there is shown an interim or temporary denture 10 which is a structural duplicate of the stent 1 comprising a base 11 having an inner surface 12, an outer surface 13 and teeth 14. With the exception of the coloration of the denture base 11 and teeth 14 to render an esthetic appearance to the denture 10, the properties of the denture 10 are like the stent 1 such that it is rendered malleable at approximately 120° F. (49° C.) thereby allowing it to be molded to fit the patient's edentulous ridge and the tooth arrangement to be altered to accommodate various intraoral variations. In the case of the denture 10, the teeth 14 are preferably made of a more rigid acrylic material and separately mounted within the base 11 so as to provide individual adjustment and better performance during use by the patient. Also, like the stent 1, the denture 10 may be applicable to full or partial maxillary and mandibular edentulous ridges.

Prior art prefabricated adjustable or moldable dentures have been made with the teeth fixed in an extra hard, non-moldable bar of rigid acrylic, or the like. As a result, the teeth were not adjustable to achieve optimum positioning and interdigitation with opposing teeth or dentures. Similarly, prior art stents, being manufactured using the standard molding and flasking methods and techniques for producing conventional dentures, included teeth which were likewise set in a rigid bar. Thus, any changes in tooth position necessitated the taking of additional impressions and the manufacture of a new stent or denture with the added time and cost involved. The present invention now provides the dentist with identical sets of fully moldable stents and dentures as well as a method for making them which overcomes the limitations of the prior art.

Figure 10:
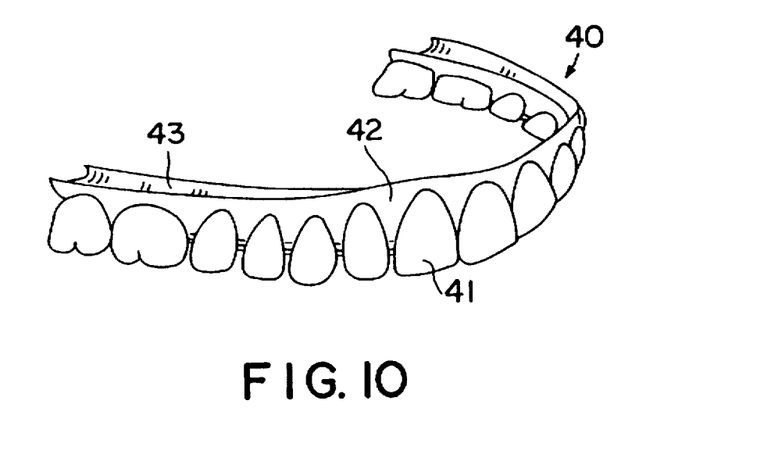
FIG. 10 is an oblique view of an alternative embodiment of the stent and temporary denture of the present invention as a prefabricated arch form for use in treating partially edentulous patients.

In an alternative embodiment illustrated in FIG. 10 and suitable for use in treating partially edentulous patients, the stent and denture are provided in an arch form 40 comprising teeth 41 and a minimal base structure 42. The arch form 40 is manufactured in the same manner and from the same materials as the full stent 1 and denture 10, the base structure 42 providing sufficient material to serve as a support for and to unite the teeth 41. Inasmuch as the arch form 40 is primarily for use in fabricating and molding stents and dentures for use in partially edentulous patients, a full base is not necessary since the partial stent and denture are positioned and held in place by conventional means used in partial prosthodontics. The arch form 40 is preferably provided in full upper and lower dental arches of varying sizes, such as that shown in FIG. 10, providing the dentist with a structure substantially corresponding to the patient's teeth and from which the appropriate segment or segments may be cut. Such partial structures are moldable in the manner described to conform to the patient's dental ridge and spacing and, when cooled, retain the configuration to which they are molded.

Figure 4A:
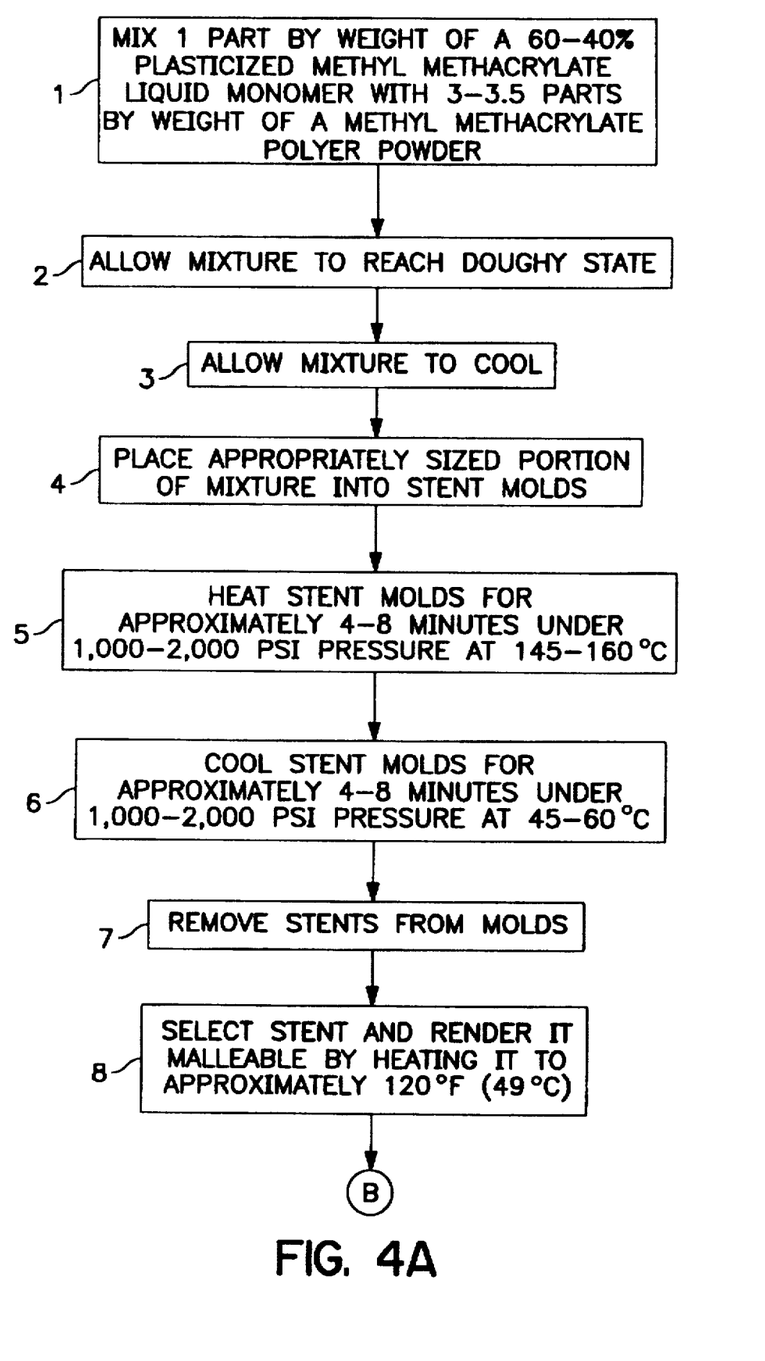
FIG. 4 is a flow chart illustrating the steps in the method of forming the stent.
Figure 4B:
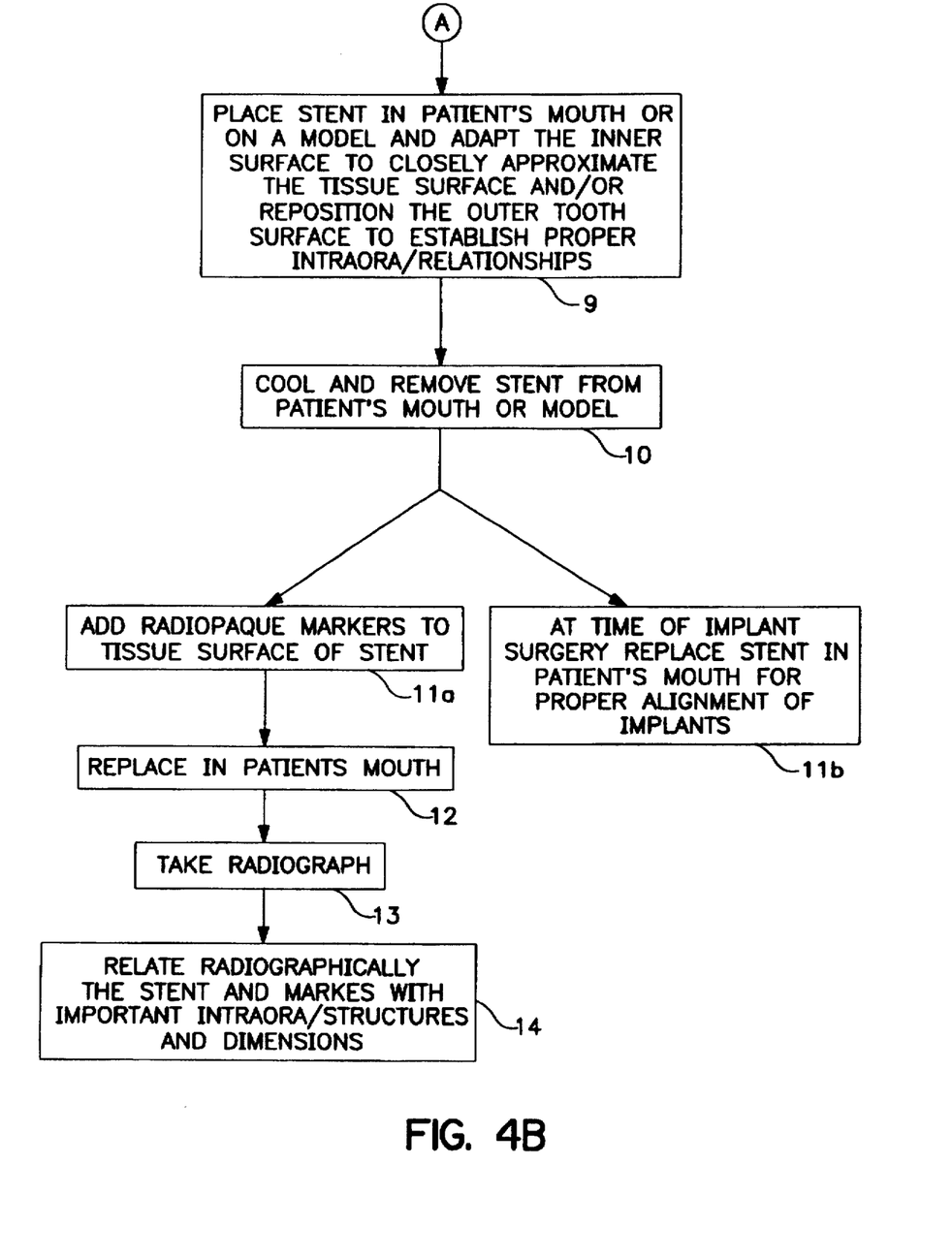

Referring now to FIG. 4, steps 1 through 7 of the flow chart illustrate the method of preparing the stent mixture and molding the mixture to form the stent. My U.S. Pat. No. 4,361,528, incorporated herein by reference, discloses a method of making a dental impression tray from a thermally deformable material substantially identical to the material used in the present invention. However, unlike the stent of the present invention, the dental impression tray of that invention is used only in an intermediate step in the conventional preparation of a conventional stent and denture; it is not part of the final permanent stent unit.

In step 1 of FIG. 4, one part by weight of a plasticized methyl methacrylate liquid monomer is mixed with 3–3.5 parts by weight of a methyl methacrylate polymer powder. In the preferred mixture, the plasticized methyl methacrylate liquid monomer is a monomer of 40–60% by weight of a methyl methacrylate liquid monomer and 40–60% by weight of a suitable liquid plasticizer such as diethyl phthalate. Also in the preferred mixture, the methyl methacrylate polymer powder has an average molecular weight of at least 650,000. Esschem Company, a Division of Sartomer Industries, Inc., P.O. Box 56, Essington, Pa. 19029 sells a suitable methyl methacrylate monomer as stock number 901 S 000, a suitable plasticizer as stock number 927 S 0000, and a suitable methyl methacrylate polymer powder as Type H003. In steps 2 and 3, the mixture is allowed to reach a doughy state and then to cool.

Although the herein-listed monomers and polymers are preferred, other materials which are thermally deformable at temperatures which are not incompatible with, or dangerous to, oral tissues and which retain their molded shape when cooled, may be used.

In steps 4–7, the doughy mixture is molded so that the tissue side approximates an edentulous ridge and the surrounding interior contours of an oral cavity and the outer surface reflects a suitable tooth arrangement. An appropriately sized portion of cooled doughy mixture is placed in each stent mold. The stent molds are then heated for approximately four to eight minutes at a temperature of 145°–160° C. and a pressure of 1000–2000 psi. After heating, the stent molds are cooled for approximately four to eight minutes at a temperature of 113°–140° F. (45°–60° C.) and a pressure of 1000–2000 psi. The cooled stents are then removed from the molds.

The number and size of the molds used to form the stents is selected so as to produce a range of final products sufficient to accommodate most patients. Sizes of small, medium and large based on anatomical averages for the population are envisioned as being sufficient for most cases although it is in no way intended that the range be limited thereto. FIG. 5 illustrates a selection of maxillary and mandibular stents or dentures based on a small 6 and 6', medium 7 and 7' and large 8 and 8' size range.

In steps 8–10, the resultant molded stents are fitted to a patient's mouth. The dentist selects an appropriately sized stent and renders it malleable by heating it to approximately 120° F. by, for example, dipping the stent into a warm water bath. The warm stent is then inserted into the patient's mouth and pressure is gently applied to attain a close approximation of the edentulous ridge and the surrounding interior contours of the oral cavity. At the same time, the outer surface 4 of the stent 1 is molded to adjust the position of the teeth 5 for optimum interdigitation and proper intraoral relationship. After this initial fitting, the stent is removed from the patient's mouth.

Referring now to step 11 in FIG. 4, an unpolymerized clear resin material may be added to line the inner surface of the stent to maximize the fitting process if called for. The stent liner may be hardened through polymerization by any of a variety of methods including light, heat or chemicals. The stent liner may be required to create and maintain a detailed intimate impression of the interior tissue surfaces of the patient's edentulous ridge and the surrounding interior contours of the mouth. Pressure is applied to the lined stent and a detailed impression of the tissue surfaces is created.

Upon removal from the patient's mouth, the liner is allowed to partially cure and, if necessary, the stent may be reinserted in the patient's mouth for additional adjustments. When the dentist is satisfied with the fitted stent, the liner is cured and hardened.

In the preferred method, a light curing unpolymerized clear resin material is provided to line the stent. Light curable resins provide greater definition and give the practitioner extended working time to perfect the fit of the liner.

The steps 1–7 shown in FIG. 4 may be adapted to the preparation of either individual stents or large quantities of stents. For mass production purposes, the dimensions of the stents may be varied to approximate the anticipated requirements of a particular population taking into account, for example, average heights and bone structures. The steps 1–7 in FIG. 4 are also used to prepare the arch form 40 stents and dentures. The same molds may be used to produce arch forms 40 in the same size selections determined for the full stents 1 and dentures 10, such as small, medium and large, as shown in FIG. 5.

The temporary or interim denture 10 is manufactured from the same material and in the same manner and sizes as the moldable stent 1. The principal differences between the stent 1 and denture 10 are the addition of a colorant to the moldable acrylic of the denture base 11 so that it esthetically resembles the natural gum tissue and the embedment in the denture base of teeth 14 which are preferably made of a more rigid acrylic and colored to match natural teeth. The method of molding and fitting the denture 10 to a patient's mouth is the same as described for molding and fitting the stent 1.

Figure 3:
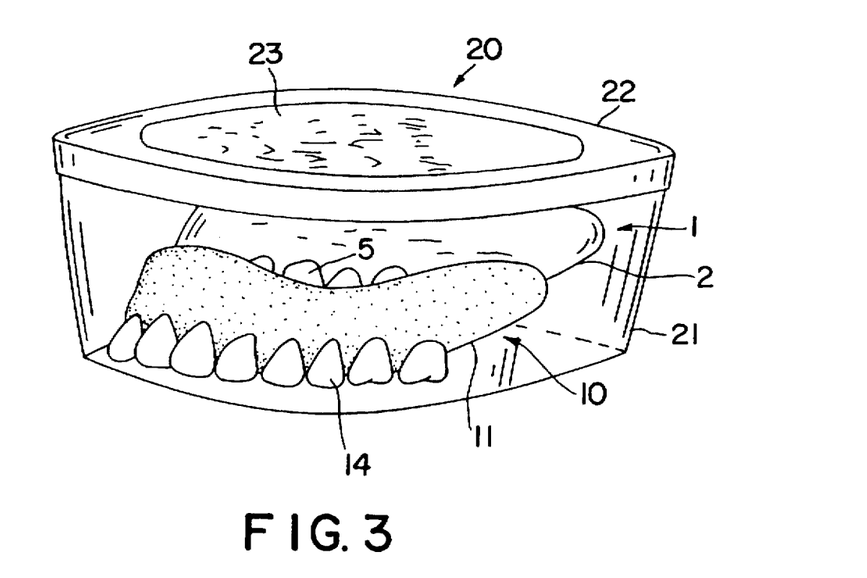
FIG. 3 shows an identical stent and denture packaged as part of a kit for use in implant prosthodontics.

FIG. 3 illustrates a simple kit 20 providing a matched set of a moldable stent 1 and a moldable temporary denture 10. As described herein, the stent 1 and denture 10 comprise identically formed bases 2 and 11 with identically sized and shaped teeth 5 and 14. The stent 1 and denture 10 are preferably packaged together in a sterile condition such as in a sealed container 21, the lid 22 of which is provided with a label 23 having indicia identifying the size of the stent 1 and denture 10, the tooth shade of the denture and other product identification. Although shown as a transparent molded plastic container 21 with a snap fit lid 22, the packaging for the kit may be any type which is sealable and sterilizable and which, preferably, indicates if any tampering has been attempted.

In addition to the stent 1 and denture 10, the kit 20 contains instructional material describing the method of heating and molding the stent 1 and denture 10. Also includable in the kit of the invention are liners of unpolymerized material which are applied to the inner surfaces of the stent and denture after initial molding and then polymerized to provide a more detailed fit with the patient's mouth tissues. Preferably, these liners remain soft and moldable until the application of a particular wavelength of light, thereby providing sufficient time for the dentist to ensure that the stent and/or denture are properly positioned for optimum interdigitation of opposing tooth surfaces. Alternatively, the unpolymerized liner material may be provided unformed for the dentist to apply and form as the circumstances warrant.

The kit may also include one or more custom moldable impression trays such as those disclosed in my U.S. Pat. Nos. 4,227,877, 4,361,528 and 4,413,979, which are incorporated herein by reference. These impression trays may be used in those circumstances where time permits or where the dentist considers it necessary to have a conventional stent and/or denture made while the patient uses the interim denture. Impression trays of this type are shown in FIGS. 6 through 9 and include a full maxillary tray 30, FIG. 6 and partial trays 31, FIGS. 7–9, which may be used in making both maxillary and mandibular impressions.

Figure 7:
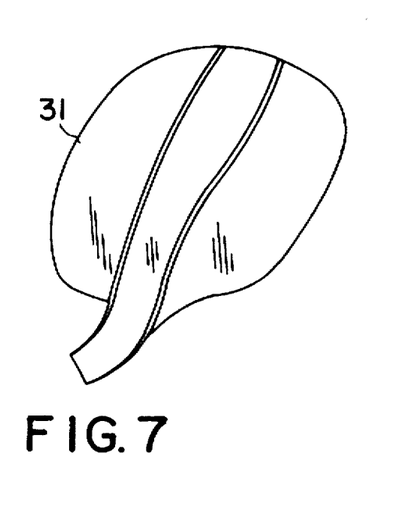
FIG. 7 shows a moldable preform for a custom partial impression tray includable as part of the kit.
Figure 8:
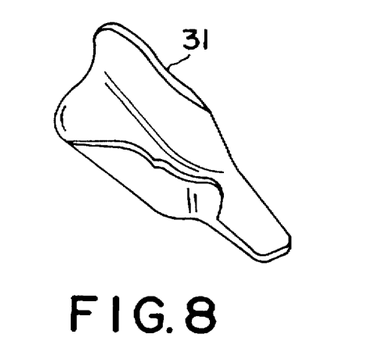
FIG. 8 shows the preform of FIG. 7 molded and ready for taking an impression.
Figure 9:
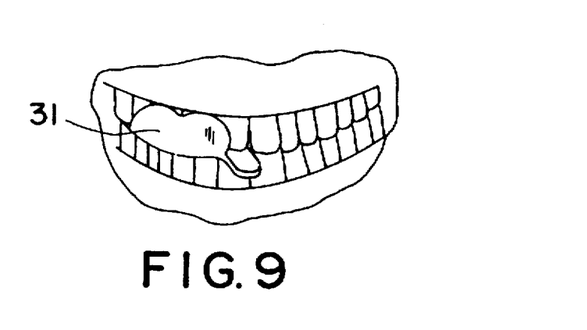
FIG. 9 depicts the impression tray of FIG. 8 in use.

Similar kits comprising matched pairs of arch forms 40 for use in treating partially edentulous patients are considered to be within the scope of this invention. Such kits preferably comprise a clear arch form for use in preparing a stent and a structurally identical colored arch form for use in preparing a matching temporary prosthesis. Instructional material, unpolymerized liner material and custom moldable impression trays are also includable in the kits. In the case of the arch form kits, the impression trays are preferably partial trays 31 such as are shown in FIGS. 7–9.

The method of use of the arch form 40 stent and temporary prosthesis is substantially identical to that recited in steps 8–11 of FIG. 4. Inasmuch as the arch form 40 is primarily for use in the treatment of partially edentulous patients, the method includes a step wherein the dentist cuts an appropriate segment from the arch form 40 stent and denture which corresponds to the partially edentulous area of the patient. These segments are heated and molded in the manner described and the stent is used for making the necessary radiographs, while the identical temporary prosthesis provides the patient with an interim prosthesis which may be secured in place using conventional techniques employed for partial dentures, crown or bridge.

To accommodate one such technique in which teeth adjacent to the edentulous segment are used as supports for the temporary prosthesis, the arch form 40 may be formed so that the teeth 42 are partially hollow inward from the ridge surface 43. In selecting the appropriate segment, the dentist includes at least one tooth at each end of the segment to fit over the corresponding teeth adjacent to the patient's edentulous portion. The patient's adjacent teeth are ground to form posts in the manner common to the preparation of dental crowns, the size of the posts corresponding to the hollow within the temporary prosthesis segment. The cavities of the remaining teeth of the temporary prosthesis segment may be backfilled, if desired, with an appropriate material to enhance their strength.

Although it is preferred to supply the needs of the dentist treating a partially edentulous patient by providing matching stents and temporary prostheses as full dental arch forms 40 from which the dentist cuts the appropriate segments, it is within the scope of this invention to also provide the stents and temporary prostheses as matching pairs of preformed segments to be molded and fit in the manner described.

The manufacture of stent and denture pairs as herein described together with the method of use and light cured acrylic polymers has the added advantage that, due to the ability to achieve accurate micro-positioning of the teeth, it is now possible to produce stents and dentures with more anatomically accurate occlusal surfaces. By molding the teeth of the stent and denture with the common 10°–30° cusp angles, more accurate interdigitation of the artificial teeth with the patient's existing teeth is achieved. This translates to a more comfortable fit for the patient as well as more efficient operating surfaces, on the denture especially, when the patient is chewing.

The above embodiments and drawings illustrate the preferred embodiments of the present invention and it is understood that many variations and modifications of those embodiments will be evident to those skilled in the art and may be carried out without departing from the spirit and scope of the present invention.

What is claimed is:

1. A clear, thermally deformable surgical and radiographic stent for the edentulous patient, said stent having an inner surface conforming to the details of an edentulous ridge and surrounding interior contour of the patient's mouth, and an outer surface conforming to the position, length, and width of teeth to be restored in a final prosthesis, said stent being formed from a thermoplastic acrylic resin which is rendered malleable when heated to a temperature above 120° F. (49° C.) whereby the stent is capable of being molded in the mouth or on a model of a patient to attain an approximation of the tissue surfaces and tooth positions.

2. The stent of claim 1 wherein the thermoplastic acrylic resin comprises one part by weight of a plasticized liquid monomer and 3–3.5 parts by weight of a methyl methacrylate polymer powder.

3. The stent of claim 2 wherein the plasticized liquid monomer comprises a mixture of 40–60% by weight of a methyl methacrylate liquid monomer and 40–60% by weight of a suitable liquid plasticizer.

4. The stent of claim 2 wherein the methyl methacrylate polymer powder has an average molecular weight of at least 650,000.

5. The stent of claim 2 wherein the acrylic resin is placed in a dental mold in the shape of an edentulous ridge and the surrounding contours of a mouth cavity, heated at 145°–155° C. for four to eight minutes under 1000–2000 psi pressure, cooled at 113°–140° F. (45°–60° C.) for four to eight minutes under 1000–2000 psi pressure, trimmed and polished to produce the molded stent.

6. The stent of claim 5 further comprising coloring agents added to the acrylic resin in a manner such that the resulting stent is opaque and has an appearance resembling natural gingival and tooth surfaces.

7. The stent of claim 1 comprising a tooth arch having molded teeth and a thermally deformable minimal base structure sufficient to support and unite said teeth from which partial segments are removable for use in partially edentulous patients.

8. A method of producing and fitting a stent, said method comprising the steps of:
providing a thermally deformable stent having an inner surface and an outer surface, said stent configured to approximate the edentulous ridge and the surrounding interior contours of a patient's mouth, said stent being made from a mixture comprising 1 part by weight of a plasticized liquid monomer and 3–3.5 parts by weight of a methyl methacrylate polymer powder,
heating the stent to above 120° F. (49° C.) to render said stent malleable,
inserting said stent in the patient's mouth and applying pressure to create a close approximation of the edentulous ridge and the surrounding interior contours of the patient's mouth in the stent,
removing the stent from the mouth, placing radiopaque markers in tissue surface of stent at ideal ridge locations, and
making a radiograph with said stent in the patient's mouth and relating the stent with its markers to intraoral bony structures.

9. The method of claim 8 wherein the plasticized liquid monomer comprises a mixture of 40–60% by weight of methyl methacrylate liquid monomer and 40–60% by weight of a suitable liquid plasticizer.

10. The method of claim 8 wherein the methyl methacrylate polymer powder has an average molecular weight of at least 650,000.

11. The method of claim 8 wherein the stent is provided to the dentist at the time of the surgical placement of implants, wherein the surgeon places the stent in the patient's mouth to determine the position of the implant relative to the position of the tooth requirements.

12. The method of claim 8 wherein the stent is lined with a polymerizable material in order to produce a more accurate fit.

13. The method of claim 8 wherein the stent is provided in segments in order to restore a partially edentulous patient.

14. The method of claim 8 wherein said stent is provided as a dental arch form comprising teeth and a minimal base structure sufficient to support said teeth, and wherein segments of said stent corresponding to the partially edentulous portion of a patient's mouth are selected from said arch for heating and molding.

15. The method of claim 8 further comprising adjusting the outer tooth form of the stent by repositioning and trimming to accommodate opposing natural or artificial occlusal surfaces.

16. The method of claim 8 comprising providing the stents in maxillary and mandibular pairs and molding occlusal tooth surfaces to create proper interocclusal dimensions and contacts.

17. The method of claim 8 wherein the stent is provided in a variety of base sizes in order to accommodate the largest number of patients.

18. The method of claim 8 wherein the stent is provided in a variety of tooth arrangements in order to accommodate the largest number of patients.

19. The method of claim 8 wherein the materials used are opaque and resemble a combination of gingival and tooth shades whereby the resulting stent is suitable for use as a temporary denture.

20. The method of claim 19 wherein the stent is provided with actual denture teeth and is relined after surgery for use as a temporary prosthesis.

21. A prosthodontic kit comprising a matched pair of a prefabricated, moldable surgical/radiographic stent and an identical prefabricated, moldable temporary denture wherein the stent and denture each comprise a base having an inner surface conforming to the details of an edentulous ridge and an outer surface conforming to the gingival surface and one or more teeth corresponding to the position, length and width of teeth to be restored by a final prosthesis, and wherein at least the base of the stent and denture is formed from a thermoplastic acrylic resin which is rendered malleable when heated to a temperature above 120° F., the thermoplastic acrylic resin comprises one part by weight of a plasticized liquid monomer and 3–3.5 parts by weight of a methyl methacrylate polymer powder, the stent is molded from a clear thermoplastic acrylic resin to facilitate visualization of underlying tissues and wherein the denture is colored to resemble the appearance of gingival tissues and teeth.

22. The prosthodontic kit of claim 21 wherein the stent and denture are each provided as a dental arch comprising teeth and a minimal base structure sufficient to support and unite said teeth, and from which segments corresponding to a partially edentulous portion of a patient's mouth are selected.

23. The prosthodontic kit of claim 21 further comprising an amount of an unpolymerized acrylic compound adapted for application to the inner surface of the stent and denture bases and capable of molding to a patient's edentulous ridge prior to polymerization.

24. The prosthodontic kit of claim 23 wherein said unpolymerized acrylic compound is a light curable acrylic.

25. The prosthodontic kit of claim 24 wherein said unpolymerized acrylic compound is provided as a preformed liner for the inner surface of the stent and denture.

26. The prosthodontic kit of claim 21 wherein the denture comprises a base of the thermoplastic acrylic resin which is rendered malleable when heated and wherein the teeth comprise denture teeth individually set in the outer surface of said base, whereby said teeth are adjustable in position relative to each other and to opposing teeth when said base is heated to malleable temperature.

27. The prosthodontic kit of claim 21 further comprising at least one custom moldable impression tray formed from a thermoplastic acrylic resin which is rendered malleable when heated to a temperature above 120° F.

28. The prosthodontic kit of claim 21 wherein said matched pair of the stent and the denture are provided in a series of sizes and tooth arrangements.

29. A method of producing and fitting a stent and a matching interim denture, said method comprising the steps of:

provinding a thermally deformable stent having an inner surface and an outer surface including representative teeth, and an identical thermally deformable temporary denture having an inner surface and an outer surface and teeth, said stent and said denture configured to approximate the edentulous ridge and surrounding interior contours of a patient's mouth, and said stent and denture being made from a mixture comprising one part by weight of a plasticized liquid monomer and 3-3.5 parts by weight of a methyl methacrylate polymer powder, heating said stent and said denture to above 120° F. to render them malleable, inserting said stent and denture separately in the patient's mouth and applying pressure to create a close approximation of the edentulous ridge and the surrounding interior contours of the patient's mouth, adjusting the relative positions of said teeth in said stent and said denture while malleable for optimum interdigitation, and allowing the stent and denture to cool.

30. The method of claim 29 further comprising applying an unpolymerized acrylic material to the inner surface of said stent and said denture and fitting said stent and denture in said mouth to obtain a detailed impression of the patient's tissue surface in said unpolymerized acrylic material and curing said acrylic material to polymerize and retain said detailed impression.

31. The method of claim 30 wherein said unpolymerized acrylic material is a light curable acrylic.

32. The method of claim 30 wherein said unpolymerized acrylic material is provided in the form of a preformed liner sized to the stent and denture.

33. The method of claim 30 wherein said stent and denture are provided as dental arch forms comprising teeth and minimal base structures sufficient to support and unite said teeth and from which identical segments corresponding to partially edentulous portions of a patient's mouth are selected and molded.

* * * * *